United States Patent [19]

Casper

[11] Patent Number: 5,382,573
[45] Date of Patent: Jan. 17, 1995

[54] HORMONE PREPARATION AND METHOD

[75] Inventor: Robert F. Casper, Toronto, Canada

[73] Assignee: Jencap Research Ltd., Toronto, Canada

[21] Appl. No.: 143,055

[22] Filed: Oct. 29, 1993

Related U.S. Application Data

[60] Division of Ser. No. 788,259, Nov. 5, 1991, Pat. No. 5,276,022, which is a division of Ser. No. 515,691, Apr. 26, 1990, Pat. No. 5,108,995, which is a continuation of Ser. No. 247,861, Sep. 22, 1988, abandoned.

[30] Foreign Application Priority Data

Sep. 24, 1987 [CA] Canada .................................. 547743
Sep. 24, 1987 [CA] Canada .................................. 547744

[51] Int. Cl.⁶ .................. A61K 31/56; A61K 31/565; A61K 31/57; A61K 31/58
[52] U.S. Cl. ..................................... 514/170; 424/449
[58] Field of Search ............................... 514/170, 171

[56] References Cited

U.S. PATENT DOCUMENTS

| | | | |
|---|---|---|---|
| 4,605,649 | 8/1986 | Liehr | 514/182 |
| 4,826,831 | 5/1989 | Plunkett et al. | 514/170 |
| 4,900,734 | 2/1990 | Maxson et al. | 514/171 |
| 4,906,169 | 3/1990 | Chien et al. | 424/448 |
| 5,023,084 | 6/1991 | Chien et al. | 424/448 |
| 5,108,995 | 4/1992 | Casper | 514/170 |
| 5,208,225 | 5/1993 | Boissonneault et al. | 514/178 |
| 5,256,421 | 10/1993 | Casper | 424/449 |
| 5,276,022 | 1/1994 | Casper | 514/170 |

Primary Examiner—Shep K. Rose
Attorney, Agent, or Firm—Evenson, McKeown, Edwards & Lenahan

[57] ABSTRACT

This invention is concerned with a contraceptive formulation and a method of contraception which employs a combination of estrogen and progestin and wherein a short period of relatively dominant estrogenic activity alternates with a short period of relatively dominant progestagenic activity. The invention also concerns a hormonal replacement formulation and method for use in menopausal or castrate women which employs a similar combination of estrogen and progestin.

26 Claims, No Drawings

HORMONE PREPARATION AND METHOD

This application is a division of my co-pending application Ser. No. 07/788,259, filed Nov. 5, 1991, now U.S. Pat. No. 5,276,022, which is a division of Ser. No. 07/515,691, filed Apr. 26, 1990, now U.S. Pat. No. 5,108,995, which is a continuation of Ser. No. 07/247,861, filed Sep. 22, 1988, now abandoned.

This invention is concerned with a contraceptive formulation and a method of contraception which employs a combination of estrogen and progestin and wherein a short period of relatively dominant estrogenic activity alternates with a short period of relatively dominant progestagenic activity. Also described are formulations which employ similar hormone combinations for hormonal replacement therapy for menopausal or castrate women.

Currently on the market there are a number of contraceptive formulations which can be classified readily into several general types. The first of these are known as monophasic formulations. These contain a constant amount of estrogen and progestin. Nuisance side effects with these pills depend on the balance between the estrogen and progestin component of the pill. For example, with a relatively dominant progestin pill, the formulation will, over time, result in a depletion of both estrogen and progestin receptors. The result which might be expected is an understimulated or atrophic endometrium which may eventually cause either on-pill amenorrhea or breakthrough bleeding or spotting due to poor epithelialization. On the other hand, with a relatively dominant estrogenic preparation, it is possible that prolonged use could result in endometrial growth with the development of unsupported fragile stroma and subsequent spotting or breakthrough bleeding.

Newer formulations known as triphasics have varying levels of estrogen and progestin; in most cases consisting of relatively constant levels of estrogen with a step-wise increase in progestin throughout the cycle. This pattern of estrogen and progestin administration results in a relatively dominant estrogenic formulation at the beginning of the package with increasing progestagenic activity toward the end of the package. Endometrial stability may be better with these pills since the estrogenic activity at the beginning of the package induces both estrogen and progestin receptors making the endometrium sensitive to the increased levels of progestin towards the end of the package. The progestin activity produces denser, more stable endometrial stroma although the relatively long duration of progestin exposure, toward the end of the package, may still lead to decreased estrogen and progestin receptors and activity. A significant problem with this type of formulation is the low dose of steroids at the beginning of the package which makes these pills vulnerable to drug interactions or missed pills which may lead to breakthrough ovulation. The beginning of the package is the critical time in terms of breakthrough ovulation since the user has just completed a 7 day drug-free interval during which follicular development may begin. Even if pregnancy does not occur, breakthrough ovulation can lead to poor cycle control.

Estrogen replacement therapy is warranted in menopausal women for several reasons. Estrogen replacement will relieve hot flushes and this relief of flushes and night sweats improves sleep patterns and contributes to the patient's general feeling of well-being (see Campbell S., Whitehead M. I. Estrogen therapy and the menopausal syndrome. In Clinics in Obstetrics and Gynecology: Volume 4. The Menopause. Edited by R. B. Greenblatt, J. W. W. Studd, London, W. B. Saunders, 1977, pages 31–47; Erlik Y., Tataryn I. V., Meldrum D. R. et al. Association of waking episodes with menopausal hot flushes. JAMA 24:1741, 1981). Estrogen replacement protects against postmenopausal loss of calcium from the skeleton, especially from vertebral bodies, preventing crush fractures and loss of body height (see Lindsay R., Hart D. M., Forrest, C. et al. Prevention of spinal osteoporosis in oophorectomized women. Lancet 2:1151, 1980). Several studies have now reported that long-term estrogen therapy is also associated with a reduction in the incidence of classical osteoporotic fractures of the forearm and hip (see Hutchinson, T. A., Polansky, S. M., Finestein, A. Postmenopausal estrogens protect against fractures of hip and distal radius. Lancet 2:706, 1979; Paganini-Hill, A., Ross, R. K., Gerkins, V. R., et al. A case control study of menopausal estrogen therapy in hip fractures. Annals of Internal Medicine 95:28, 1981; Weiss N. S., Ure C. L., Ballard J. H. et al. Decreased risk of fractures of the hip and lower forearm with postmenopausal use of estrogen. New England Journal of Medicine 303:1195, 1980). Another beneficial effect of long-term estrogen use is the reduction of the risk of death from ischemic heart disease probably mediated by changes in blood lipoprotein concentrations (see Ross R. K., Paganini-Hill A., Mack T. M. et al. Menopausal estrogen therapy and protection from ischemic heart disease. Lancet 1:858, 1981). Estrogen replacement has also been shown to improve the vascularity and health of the vaginal mucosa and urinary tract. The only major risk factor associated with estrogen administration in the doses required to relieve menopausal symptoms, is hyperstimulation of the endometrium and an increased risk of endometrial cancer (see Cramer D. W., Knapp R. C. Review of epidemiologic studies of endometrial cancer and exogenous estrogen. Obstetrics and Gynecology 54:521, 1979; Shapiro S., Coughman D. W., Sloan D., et al. Recent and past use of conjugated estrogens in relation to adenocarcinoma of the endometrium. New England Journal of Medicine 303:485, 1980).

Estrogens predispose to cancer of the endometrium by stimulating cell mitosis and proliferation and increasing the levels of DNA synthesis and nuclear estradiol receptors in the endometrium (see Whitehead M. I., Townsen P. T., Pryce-Davies J., et al. Effects estrogens and progestins on the biochemistry and morphology of the postmenopausal endometrium. New England Journal of Medicine 305:1599, 1981; Whitehead M. I., Townsen P. T., Pryce-Davies J., et al. Actions of progestins on the morphology and biochemistry of the endometrium of postmenopausal women receiving low dose estrogen therapy. American Journal of Obstetrics and Gynecology, 142:791, 1982).

The addition of a progestin for 13 days each month has been demonstrated to protect the endometrium from these stimulatory effects of estrogen (see Gambrill R. D., Jr., Massey F. M., Castaneda et al. Use of the progestogen challenge test to reduce the risk of endometrial cancer. Obstetrics and Gynecology 55:732, 1980; Studd J. W. W., Thom M. H., Patterson M. E. L., Wade-Evans T. The prevention and treatment of endometrial pathology in postmenopausal women receiving exogenous estrogens. In: Pasetto N., Paoletti R., Armbus J. L., Editors. The menopause and postmenopause. Lancester MPT Press. 127,1980).

The addition of a progestin protects the endometrium by reducing nuclear estradiol receptor concentration and thereby decreases nuclear estrogen bioavailability resulting in an antimitotic effect and lowering DNA synthesis. Progestins also increase the activity of endometrial estradiol-17beta-dehydrogenase, an enzyme which metabolizes estradiol to estrone, a less potent estrogen (see Whitehead M. I., Townsen P. T., Pryce-Davies J. Effects of estrogens and progestins on the biochemistry and morphology of the postmenopausal endometrium. New England Journal of Medicine. 305:1599, 1981; King R. J. B., Townsen P. T., Sittle N. C., et al. Regulation of estrogen and progesterone receptor levels in epithelium and stroma from pre and postmenopausal endometria. Journal of Steroids and Biochemistry, 16:21, 1982; Gurpide E. Enzymatic modulation of hormonal action at the target tissue. Journal of Toxicology and Environmental Health, 4:249, 1978). The addition of progestin to estrogen replacement therapy may also result in an increase in bone mass when started within 3 years of the menopause (see Nachtigall L. E., Nachtigall R. H., Nachtigall R. D., et al. Estrogen replacement therapy: A 10 year prospective study in relationship to osteoporosis. Obstetrics and Gynecology 53:277, 1979; Lindsay R., Hart D. M., Forrest C., et al. Prevention of spinal osteoporosis in oophorectomized women. Lancet 2:1151, 1980). However, concerns have been expressed about the potential adverse effects of progestin in suppressing high density lipoprotein cholesterol concentrations (see Hirvonen E., Malkonen M., Manninen V. Effects of different progestogens on lipoproteins during postmenopausal replacement therapy. New England Journal of Medicine 304:560, 1981). This cholesterol fraction appears to have a protective effect against ischemic heart disease and atherosclerosis. The lowering of HDL cholesterol by progestin could negate the long-term beneficial effects of estrogen in reducing the incidence of myocardial infraction. Other side effects of progestins include acne, breast tenderness, depression and irritability (see Barranco V. P. Effect of androgen dominant and estrogen dominant oral contraceptives on acne. Cutis 14:384, 1974; Royal College of General Practioners. Oral Contraceptives and Health: An Interim Report. New York: Pitman, 1974). Since the side effects of progestins appear to be dose dependent, the dose of progestin used with postmenopausal estrogen replacement should be the minimum necessary to achieve endometrial protection. (see Padwick M. L., Pryce-Davies J., Whitehead M. I. A simple method for determining the optimal dosage of progestin in postmenopausal women receiving estrogens. New England Journal of Medicine 315:930, 1986).

The biological effects of both estrogen and progestin in target tissues such as the endometrium are dependent on the levels of estrogen and progestin receptors. Both estrogen and progestins exert a modulating influence on the levels of their own receptors. For example, in the luteal phase of the menstrual cycle, serum progesterone levels increase and progesterone mediated secretory changes occur in the uterine endometrium. The presence of progesterone receptors has been shown to be a necessary prerequisite for progesterone action in the endometrium (see Walters M. R. and Clark J. H. Relationship between the quantity of progesterone receptors and the antagonism of estrogen-induced uterotropic response. Endocrinology 105:382, 1979) and it is well documented that estrogen priming in the follicular phase of the cycle is responsible for the development of both estrogen and progesterone receptors (see Bayard F., Damilano S., Robel P. and Baulieu E. E. Cytoplasmic and nuclear estradiol and progesterone receptors in human endometrium. Journal Clinical Endocrinology and Metabolism 46:635, 1978). On the other hand, progesterone exerts a negative feedback effect on its own receptor (see Tseng L. and Gurpide E. Effects of progestins on estradiol receptor levels in human endometrium. Journal Clinical Endocrinology and Metabolism 41:402, 1975) and also acts to downregulate endometrial estrogen receptors possibly by induction of an estrogen receptor regulatory factor (see Leavitt W. W., Okulicz W. C., McCracken J. A., Schramm W. S. and Robidoux W. F., Jr. Rapid recovery of nuclear estrogen receptor and oxytocin receptor in the ovine uterus following progesterone withdrawal. Journal Steroid Biochemistry 22:686, 1985).

These physiologic changes can be reproduced pharmacologically as shown by the induction of estrogen and progestin receptors in postmenopausal women by the administration of ethinyl estradiol (see Kreitmann B., Bugat R. and Bayard F. Estrogen and progestin regulation of the progesterone receptor concentration in human endometrium. Journal Clinical Endocrinology and Metabolism 49:926, 1979). Neumannova et al. (see Short-term effects of tamoxifen, medroxyprogesterone acetate, and their combination on receptor kinetics and 17beta-hydroxysteroid dehydrogenase in human endometrium. Obstetrics and Gynecology 66:695, 1985) have also demonstrated that administration of medroxyprogesterone acetate in estrogen-primed women decreases the concentration of endometrial progestin receptors while at the same time increasing the activity of 17beta-hydroxysteroid dehydrogenase, the enzyme which is responsible for metabolism of estradiol to the less potent estrone.

A complex interaction occurs between estrogen and progesterone or progestin in the human endometrium with the progestins acting as anti-estrogens. Estrogen and progestin interactions are also dynamic. For example, estrogen administration increased the concentration of both estrogen and progestin receptors to peak levels, 7 times above baseline, within 3 days (see Ekert R. L. and Katzenellenbogen B. S. Human endometrial cells in primary tissue culture: Modulation of the progesterone receptor level by natural and synthetic estrogens in vitro. Journal Clinical Endocrinology and Metabolism 52:699, 1981). A three-fold increase in receptor concentrations occurred within one day. Normal physiologic levels of progesterone in the first 3 days of the luteal phase resulted in a rapid and significant decrease in estrogen receptor number (see Kreitmann-Gimbal B., Bayard F., Nixon W. E. and Hodgen G. D. Patterns of estrogen and progesterone receptors in monkey endometrium during the normal menstrual cycle. Steroids 35:471, 1980). Exogenous administration of progesterone to cynomolgous macaques significantly suppressed estrogen receptors within 1 to 2 days (see West N. B. and Brenner R. M. Progesterone-mediated suppression of estradiol receptors in cynomolgous macaque cervix, endometrium and oviduct during sequential estradiol-progesterone treatment. Journal Steroid Biochemistry 22:29, 1985) and medroxyprogesterone acetate was able to significantly suppress progestin receptor levels in premenopausal women within 4 hours (see Neumannova M., Kauppila A., Kivinen S. and Vihko R. Short-term effects of tamoxifen, medroxyprogesterone acetate, and their combination on receptor kinetics and 17beta-hydroxysteroid dehydrogenase in human endometrium, Obstetrics and Gynecology 66:695, 1985). In contrast, progesterone withdrawal in the presence of constant estrogen levels has been shown to result in rapid (6 to 12 hours) recovery of nuclear estrogen receptors in sheep endometrium, associated with an estrogen induced biological response, i.e. production of oxytocin receptors (see Leavitt W. W., Okulicz W. C., McCracken J. A., Schramm W. S. and Robidoux W. F.: Jr. Rapid recovery of nuclear estrogen receptor and oxytocin receptor in the ovine uterus following progesterone withdrawal. Journal Steroids and Biochemistry 22:686, 1985). A similar phenomenon occurs in pregnant guinea pigs when estrogen levels rise relative to progesterone levels prior to parturition (Biology and Reproduction 22:1106, 1980) see Alexandrova, M. and Soloff, M. S. Oxytocin receptors and parturition in the guinea pig.

Therefore, it appears that estrogen acts to stimulate both estrogen and progestin receptor concentrations and to induce sensitivity of the endometrium to both estrogen and progestin. Progesterone or progestin exerts an anti-estrogen action by decreasing the concentration of estrogen receptors and by increasing 17beta-hydroxysteroid dehydrogenase activity in endometrial tissue. However, it appears that the stimulatory effects of progesterone on human endometrial function are of short duration probably because of a self-provoked downregulation of progestin receptors (see Neumannova M., Kauppila A., Kivinen S. and Vihko R. Short-term effects of tamoxifen, medroxyprogesterone acetate, and their combination on receptor kinetics and 17beta-hydroxysteroid dehydrogenase in human endometrium, Obstetrics and Gynecology 66:695, 1985; Whitehead M. I., Townsen P. T., Pryce-Davies J. et al. Effects of estrogens and progestins on the biochemistry and morphology of the postmenopausal endometrium. New England Journal of Medicine. 305:1599, 1981). For example, the effect of progesterone on 17beta-hydroxysteroid dehydrogenase peaks at 3 days and is then followed in 2 to 3 weeks by suppression of the enzyme (see Whitehead M. I., Townsend P. T., Pryce-Davies J. et al. Effects of estrogens and progestins on the biochemistry and morphology of the postmenopausal endometrium. New England Journal of Medicine 305:1599, 1981).

Current hormonal replacement consists of continuous (daily or cyclic) (example days 1-25 of each month) estrogen administration with the addition of a progestin for 10-13 days (example days 13-25) each month. This type of replacement regimen is effective in preventing menopausal symptoms and at the same time, protects the endometrium against the development of hyperplasia or adenocarcinoma. However, the cyclic administration of a progestin leads to a scheduled withdrawal bleed or period in 65-75% of women (see Hellberg D., Nilsson S. Comparison of a triphasic estradiol/norethisterone acetate preparation with and without estriol component in the treatment of climacteric complaints; Maturitas 5:233, 1984: Christensen M. S., Hagen C., Christiansen C., Transbol I. Dose response evaluation of cyclic estrogen/gestagen in postmenopausal women: Placebo controlled trial of its gynecologic and metabolic actions. American Journal of Obstetrics and Gynecology. 144:873, 1982). This withdrawal bleeding is usually not welcomed by the patient and can lead to problems with compliance. Also because the progestin administration is preceded by up to 13-16 days of unopposed estrogen therapy with endometrial proliferation and estrogen and progestin receptor induction, it is possible that a high dose of progestin is required to antagonize these effects resulting in a greater chance of side effects and adverse metabolic effects. Newer continuous low dose estrogen and progestin regimens for hormonal replacement may avoid the problem of withdrawal bleeding (see Magos A. L., Brincatt M., O'Dowd T., et al. Amenorrhea and endometrial atrophy following continuous oral estrogen and progestogen therapy in postmenopausal women. Maturitas 6:145, 1984). However, daily administration of a progestin in these regimens induces depletion of both estrogen and progestin receptors resulting in endometrial atrophy which may be associated with breakthrough bleeding. Since abnormal bleeding in a postmenopausal woman is known to be associated with endometrial carcinoma, it must be investigated by endometrial sampling for hypertrophy usually by D&C. Daily administration of a progestin also raises the concern that the favourable effects of estrogen on HDL cholesterol metabolism will be adversely affected with a fall in HDL cholesterol (see Notelovitz M., Gudat J. C., Ware M. D., Dougherty M. C. British Journal of Obstetrics and Gynecology. 90:171, 1983).

The present invention provides a pharmaceutical preparation for administration to a female of child bearing age or older in whom ovarian estrogen and progesterone production has been interrupted either because of natural menopause, surgical, radiation, or chemical ovarian ablation or extirpation or premature ovarian failure, which comprises a plurality of unit dosages, each unit dosage for continuous consecutive daily administration and comprising combinations of estrogen and progestin selected from a combination with relatively dominant estrogen activity and a combination with relatively dominant progestin activity, with a plurality of dominant estrogen dosages being alternated with plurality of dominant progestin dosages, and each unit dosage also comprising a pharmaceutically acceptable inert carrier when required.

In another aspect, the invention provides a method of hormonal replacement therapy for administration to a female in need of such treatment, in particular to a female of child bearing age or older in whom ovarian estrogen and progesterone production has been interrupted either because of natural menopause, surgical, radiation, or chemical ovarian ablation or extirpation or premature ovarian failure, which comprises administering continuously and consecutively, in daily sequence, a plurality of daily unit dosages comprising combinations of estrogen and progestin, selected from a combination with relatively dominant estrogen activity and a combination with relatively dominant progestin activity, a plurality of the dominant estrogen activity unit dosages being alternated with a plurality of the dominant progestin activity unit dosages.

The hormonal replacement formulation of the present invention results in the absence of withdrawal bleeding; intermittent increases in estrogen activity; and stimulation of endometrial growth and progestin receptors. The previously described push/pull activity not only keeps endometrial activity within a narrow range depending on the number of days of estrogenic and progestagenic activity, but also maintains a stable endometrium resulting in the absence of breakthrough or withdrawal bleeding.

This hormonal replacement formulation allows better progestational effects with less progestin. With the current formulation the dose of progestin is significantly decreased compared with a preparation containing constant daily administration of a progestin. A total steroid dosage is achieved which is similar to or even lower than that of thee present cyclic method of administering estrogen and progestin for hormonal replacement therapy of ovarian failure.

The estrogens which may be employed as a component in the regimens of this invention may be any of those conventionally available. Typically, the estrogen may be selected from the group comprising synthetic and natural estrogens. The synthetic estrogens may be selected from, for example, ethinyl estradiol, mestranol and quinestranol. Particularly of interest are 17alpha-ethinylestradiol and esters and ethers thereof. The preferred estrogen is 17alpha-ethinylestradiol. The natural estrogens may include, for example, conjugated equine estrogens, estradiol-17beta, estradiol valerate, estrone, piperazine estrone sulphate, estriol, estriol succinate, and polyestrol phosphate.

The progestin component may be any progestationally active compound. Thus, the progestin may be selected from progesterone and its derivatives such as, for example, 17-hydroxy progesterone esters, 19-nor-17-hydroxy progesterone esters, 17alpha-ethinyltestosterone and derivatives thereof, 17alpha-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone, dl-norgestrel, d-17alpha-acetoxy-13beta-ethyl-17alpha-ethinyl-gon-4-en-3-one oxime, cyproterone acetate, desogestrel and norgestimate. Preferred progestins are norethindrone, d-norgestrel and norgestimate.

In a preferred form of the invention, the plurality of dosages may comprise from one to five unit dosages, but preferably three unit dosages are employed. Thus, in a preferred form of the invention, three unit dosages of relatively dominant estrogen activity are alternated with three unit dosages of relatively dominant progestin activity and so on for a total of twenty-one or twenty-four unit dosages. Four or seven unit dosages which are free of hormone are included to approximate the natural twenty-eight day menstrual cycle of the female. These pills may comprise a placebo or any other hormone-free agent. Examples of suitable alternative agents include vitamins, such as iron supplements. Where the total unit dosages do not comprise multiples of three, an appropriate number of hormone-free unit dosages may be included to make up the total required units.

Generally, the quantities of estrogen and progestin incorporated in the formulation of the invention are dependent on the type of estrogen or progestin selected. However, the quantities employed are generally less than those used in the currently marketed formulations for reasons mentioned earlier. In preferred formulations, the estrogen level is kept constant, while the progestin level is adjusted up or down to produce the required estrogen or progestin dominance. The selection of quantity is dependent on the type of estrogen or progestin since each hormone has its own specific activity.

Typically in the hormone replacement formulations, the amount of estrogen per unit dose may range from a minimum of about 0.3 mg of estrone sulphate or its equivalent to a maximum of about 2.5 mg of estrone sulphate or its equivalent. The amount of progestin per unit dosage may range from a minimum of 0 mg to a maximum of about 5 mg of norethindrone or its equivalent.

Some preferred combinations include the following:
1. Three units dosages of 0.75 mg piperazine estrone sulphate alternating with three unit dosages of 0.75 mg of piperazine estrone sulphate with 0.35 mg of norethindrone.
2. Three unit dosages of 0.75 mg piperazine estrone sulphate and 0.15 mg of norethindrone alternating with three unit dosages of 0.75 mg of piperazine estrone sulphate and 0.35 mg of norethindrone.

The above combinations may also be grouped into three's and four's, starting with either three or four day groups and ending with the other.

The formulations of the invention may be administered orally, preferably in tablet form, parenterally, sublingually, transdermally, intravaginally, intranasally or buccally. The method of administration determines the types of estrogens and progestins useful in the formulation, as well as the amounts per unit dosage.

Methods for transdermal administration including the associated methods for manufacturing such systems are well known in the art. In this connection, reference may be had to U.S. Pat. Nos. 4,752,478, 4,685,911, 4,438,139 and 4,291,014.

Generally speaking, the formulations are prepared according to conventionally known procedures in accordance with the method of administration. Thus, the active ingredients are prepared according to known methods in a pharmaceutically acceptable form for administration. These ingredients, in their required quantities are combined with the appropriate pharmaceutical carriers such as additives, vehicles and/or flavour ameliorating substances. These substances may be referred to as diluents, binders and lubricants. Gums, starches and sugars are also common terms. Typical of these types of substances or excipients are pharmaceutical grades of mannitol, lactose starch, magnesium stearate, sodium saccharin, talcum, cellulose, glucose, sucrose, magnesium carbonate and the like. The active ingredient(s) may comprise from about 0.01% by weight to about 99.99% by weight of the total formulation and the remainder comprises the pharmaceutically acceptable carrier. The percentage of active ingredient(s) may vary according to the delivery system or method of administration and is chosen in accordance with conventional methods known in the art.

Thus, the active ingredients are compounded with the chosen carrier and in for example the case of a tablet form, placed in a tablet molding apparatus to form the tablets which are subsequently packaged in accordance with the chosen regimen.

In the oral form of the formulation, the contraceptives are preferably produced in the form of a pharmaceutical kit or package, with the daily dosages arranged for proper sequential administration. Thus, in another aspect, the present invention also provides a pharmaceutical package which contains combination-type contraceptives in multiple dosage units in a synchronized, fixed sequence, wherein the sequence or arrangement of the dosage units corresponds to the stages of daily administration.

Preferably, such packages are in the form of a transparent package with twenty-eight dosage units arranged sequentially and consisting of twenty-one or twenty-four tablets containing the combined estrogen/progestin formulation set up for the cyclical regimen of the invention and seven or four placebos thereafter.

Preferably the placebo tablets and tablets containing the hormones are different colours or shapes. Data indications may be provided on the packaging. The packaging may be a tube or box or a strip. The box may be circular, square, or otherwise shaped with the tablets being accommodated separately therein for ease of administration. Date indications may appear adjacent each tablet corresponding with the days on which each tablet is to be taken. Some indication of the sequence in which the tablets are to be taken preferably appears on the packaging regardless of its form.

In the following examples, specific embodiments of the present invention are set forth. These are meant to be illustrative of the invention and are not meant to limit it in any way. All parts and percentages are by weight, unless indicated otherwise.

EXAMPLES ILLUSTRATING THE METHOD OF CONTRACEPTION

Example 1

Three-day phases of unit dosages of 17alpha-ethinylestradiol(EE) 0.035 mg. and norethindrone (NET) 0.5 mg. alternating with three-day phases of unit dosages of EE 0.035 mg. and NET 0.75 mg. for a total of 7 phases (21 days or 21 unit dosages) beginning and ending with the NET 0.5 mg. combination.

Example 2

Three-day phases (unit dosages of EE 0.035 mg. and NET 0.5 mg.) alternating with three-day phases of EE 0.035 mg. and NET 0.35 mg., beginning and ending with the 0.5 mg. combination

Example 3

Two-day phases of unit dosages of EE 0.035 mg alternating with unit dosages of EE 0.035 mg and NET 0.35 mg, beginning and ending with the first unit dosage and running for 24 days total.

Example 4

Three-day phases of unit dosages of EE 0.035 mg and NET 0.15 mg alternating with EE 0.035 mg and NET 0.35 mg and running for 24 days total.

Example 5

Three-day and four-day phases of each of the above combinations as set forth in Examples 1 and 2, starting with either three or four-day phases and ending with the other.

Example 6

Four-day and three-day phases are prepared, starting with a four-day unit dosage of 0.5 rag. NET and 0.035 mg. EE and ending with 0.75 mg. NET and 0. 035 mg. EE.

Example 7

Three-day and four-day phases of formulations starting with a three-day phase of 0.35 mg. NET with 0.035 mg. EE and ending with a four-day phase of 0.5 mg. NET and 0. 035 mg. EE.

Example 8

One-day alternating phases using the unit dosages set forth in Examples 1 and 2.

Example 9

Two-day alternating phases ending or beginning with a single three-day phase, using the unit dosage formulations set forth in Examples 1 or 2.

Example 10

Three-day phases of EE 0.035 mg. and levo-norgestrel (D-norgestrel) 0.05 mg. alternating with 3-day phases of EE 0.035 mg. and levonorgestrel 0.075 mg.

Example 11

Three-day phases of EE 0.035 mg. and norgestimate 0.05 mg. alternating with EE 0.035 mg. and norgestimate 0.075 mg.

Example 12

Three-day phases of EE 0.035 mg. and norgestimate 0.05 mg. alternating with EE 0.035 and norgestimate 0.035 mg.

Examples 13 & 14

One formulation was administered to two women for a total of three cycles to establish that cycle control, in terms of breakthrough bleeding, is acceptable. The test formulation consisted of three unit dosages of 0.035 mg. of 17alpha-ethinylestradiol and 0.5 mg. of norethindrone alternating with three unit dosages of 0.035 mg. of 17alpha-ethinylestradiol and 0.75 mg. of norethindrone for a total of seven groups of three, beginning and ending with the 0.5 mg. of norethindrone combination.

Example 13

A twenty-three year old nulliparous woman who had not taken any hormonal formulation including oral contraceptives for three months agreed to take the test formulation of the invention for two cycles. The subject was in good health and did not smoke. The subject had no contraindications to the use of oral contraceptives and her menstrual cycles were regular. The subject started the test formulation on the fifth day of her cycle (onset of menstruation is considered day 1) for twenty-one consecutive days (first cycle), followed by a seven day interval which was free of any hormone and then restarted the test formulation for another twenty-one days (second cycle). In the first cycle the subject had no bleeding or spotting while taking the test formulation and had a withdrawal bleed starting on the second day of the hormone free interval. The withdrawal bleed lasted for five days and was lighter than a normal menstrual period consisting of reddish-brown spotting. There was no discomfort associated with the withdrawal bleeding. In the second cycle, the subject was also free of bleeding or spotting while taking the test formulation and again had a brownish, very light withdrawal bleed which began two days after stopping the test formulation and lasted for six days. The subject experienced no side effects during the two test cycles.

Example 14

The subject was a healthy, twenty-seven year old nulliparous woman who was currently taking a commercially available oral contraceptive formulation containing 17alpha-ethinylestradiol and dl-norgestrel (Tripbasil (Trade mark of Wyeth Pharmaceuticals)). The subject agreed to take the test formulation of the invention for one cycle. The subject started the test formulation after a seven day hormone free interval following the last Tripbasil tablet. The test formulation was taken for twenty-one days followed by a seven day drug free interval. The subject had no spotting or bleeding during the time she took the test formulation and experienced a withdrawal bleed which began two days after stopping the test formulation. The withdrawal bleeding lasted four days, was painless and was the same amount and colour as a normal menstrual period for the subject. The subject had no side effects during the test formulation.

Both subjects found the test formulation to be acceptable in terms of cycle control, side effects and menstrual bleeding.

EXAMPLES ILLUSTRATING THE HORMONE-REPLACEMENT THERAPY

Example 15

Three-day phases of unit dosages of 0.75 mg piperazine estrone sulphate alternating with three-day phases of unit dosages of estrone sulphate 0.75 mg and NET 0.35 mg given continuously or orally.

Example 16

Three-day phases (unit dosages of estrone sulphate 0.75 mg and norethindrone 0.15 mg) alternating with three-day phases of estrone sulphate 0.75 mg and norethindrone 0.35 mg given continuously or orally.

Example 17

Three-day phases of oral micronized 17betaestradiol 1 mg alternating with three-days of 17beta-estradiol 1 mg and norethindrone 35 mg.

Example 18

Three-day phases of transdermal 17beta-estradiol (100 µg/day) alternating with three-days of transdermal 17beta-estradiol (100 µg/day) and transdermal norethindrone (0.35 mg/day) given continuously.

Example 19

Three-day phases of estrone sulphate 1.25 mg alternating with three-day phases of estrone sulphate 1.25 mg and norethindrone 0.35 mg given continuously or orally.

Example 20

Three-day phases of estrone sulphate 1.25 mg alternating with three-day phases of estrone sulphate 1.25 mg and norethindrone 0.5 mg given continuously or orally.

Example 21

One-day or two-day alternating phases using the unit dosages set forth in Examples 15 and 16 given continuously or orally.

Example 22

Three-day phases of estrone sulphate 0.75 mg alternating with three-day phases of estrone sulphate 0.75 mg and norgestimate 0.050 mg given continuously or orally.

Example 23

Three-day and four-day phases of each of the combinations as set forth in Examples 13 and 14, starting with either a 3- or 4-day phase and given continuously or orally.

Example 24

Two-day and three-day phases of each of the combinations as set forth in Examples 15 and 16, starting with either a two- or three-day phase and given continuously or orally.

Example 25

A pharmaceutical preparation is prepared in which three days of transdermal 17β-estradiol (0.1 mg/day) with norethindrone (0.15 mg/day) are alternated with transdermal 17-estradiol (0.1 mg/day) with norethindrone (0.35 mg/day).

While the present invention has been described with reference to specific embodiments thereof, it should be understood by those skilled in the art that various changes may be made and equivalents may be substituted without departing from the true spirit and scope of the invention. In addition, many modifications may be made to adapt a particular situation, material or composition of matter, process, process step or steps, or then present objective to the spirit of this invention without departing from its essential teachings.

The embodiments of the invention in which an exclusive property or privilege is claimed are defined as follows:

1. A pharmaceutical preparation for administration to a female in need of hormone replacement therapy comprising repeating cycles of a pharmaceutical regimen, each cycle comprising a series of from twenty to thirty-five consecutive daily unit doses arranged in alternating estrogen dominant phases and progestin dominant phases, each phase consisting of from one to four consecutive daily unit doses, wherein the daily unit doses of said estrogen dominant phases contain
   i) an amount of a substance exhibiting estrogen activity or
   ii) an amount of a substance exhibiting estrogen activity and an amount of a substance exhibiting progestin activity, and the daily unit doses of said progestin dominant phases contain an amount of a substance exhibiting estrogen activity and an amount of a substance exhibiting progestin activity, the amount of said substance exhibiting progestin activity being alternately increased in the progestin dominant phases to provide daily unit doses exhibiting progestin dominant activity and decreased in the estrogen dominant phases to provide daily unit doses exhibiting estrogen dominant activity, and wherein the amount of substance exhibiting estrogen activity per unit dose exhibits an estrogen activity equivalent to from about 0.3 to about 2.5 mg of piperazine estrone sulfate, and the amount of substance exhibiting progestin activity per unit dose ranges from 0 to an amount which exhibits a progestin activity equivalent to about 5 mg of norethindrone.

2. A pharmaceutical preparation according to claim 1 wherein the daily unit doses of said estrogen dominant phases contain an amount of substance exhibiting progestin activity ranging from 0 to an amount which exhibits a progestin activity equivalent to 0.5 mg of norethindrone, and the daily unit doses of said progestin dominant phases contain an amount of substance exhibiting progestin activity which exhibits a progestin activity equivalent to from 0.35 to 5 mg norethindrone, the amount of substance exhibiting progestin activity being greater in said progestin dominant phases than in said estrogen dominant phases.

3. A pharmaceutical preparation according to claim 1, wherein all of said daily unit doses contain a uniform amount of said substance exhibiting estrogen activity.

4. A pharmaceutical preparation according to claim 1, wherein the daily unit doses of said estrogen dominant phases are free of substance exhibiting progestin activity.

5. A pharmaceutical preparation according to claim 1, wherein said substance exhibiting estrogen activity is selected from the group consisting of 17α-ethinyl estradiol, 17β-estradiol, 17β-estradiol valerate, conjugated equine estrogens, piperazine estrone sulfate, and estropipate, and said substance exhibiting progestin activity is selected from the group consisting of norethindrone, desogestrel, levo-norgestrel, norgestimate, progesterone, medroxy-progesterone acetate, gestodene, and cyproterone acetate.

6. A pharmaceutical preparation according to claim 1, wherein said daily unit doses are in a form selected from the group consisting of orally administrable form, transdermally administrable form, and buccally administrable form.

7. A pharmaceutical preparation according to claim 1, comprising a series of consecutive daily unit doses arranged in estrogen dominant phases of two daily unit doses each alternating with progestin dominant phases of two daily unit doses each.

8. A pharmaceutical preparation according to claim 1, comprising a series of consecutive daily unit doses arranged in estrogen dominant phases of three daily unit doses each alternating with progestin dominant phases of three daily unit doses each.

9. A pharmaceutical preparation according to claim 1, wherein said preparation is a hormone replacement therapy preparation, and each of said daily unit doses contains an amount of substance exhibiting estrogen activity which exhibits an estrogen activity equivalent to from 0.3 to 2.5 mg of piperazine estrone sulfate, and an amount of substance exhibiting progestin activity ranging from 0 to an amount which exhibits a progestin activity equivalent to 5 mg norethindrone.

10. A pharmaceutical preparation according to claim 9, wherein each estrogen dominant phase consists of three orally administrable daily unit doses each containing 0.75 mg piperazine estrone sulfate, and each progestin dominant phase consists of three orally administrable daily unit doses each containing 0.75 mg piperazine estrone sulfate and 0.35 mg norethindrone.

11. A pharmaceutical preparation according to claim 9, wherein each estrogen dominant phase consists of three transdermally administrable daily unit doses each releasing 0.1 mg 17β-estradiol, and each progestin dominant phase consists of three transdermally administrable daily unit doses each releasing 0.1 mg 17β-estradiol and 0.35 mg norethindrone.

12. A pharmaceutical preparation according to claim 9, wherein each estrogen dominant phase consists of three transdermally administrable daily unit doses each releasing 0.1 mg 17β-estradiol and 0.15 mg norethindrone, and each progestin dominant phase consists of three transdermally administrable daily unit doses each releasing 0.1 mg 17β-estradiol and 0.35 mg norethindrone.

13. A pharmaceutical preparation according to claim 9, wherein three unit doses of 1.0 mg of 17-estradiol are alternated with three unit doses of 1.0 mg of 17-estradiol and 0.35 mg norethindrone.

14. A pharmaceutical package containing a least one cycle of a pharmaceutical regimen for administration to a female in need of hormone replacement therapy, each said cycle comprising repeating cycles of a pharmaceutical regimen, each cycle comprising a series of from twenty to thirty-five consecutive daily unit doses arranged in alternating estrogen dominant phases and progestin dominant phases, each phase consisting of from one to four consecutive daily unit doses, wherein the daily unit doses of said estrogen dominant phases contain i) an amount of a substance exhibiting estrogen activity or ii) an amount of a substance exhibiting estrogen activity and an amount of a substance exhibiting progestin activity, and the daily unit doses of said progestin dominant phases contain an amount of a substance exhibiting estrogen activity and an amount of a substance exhibiting progestin activity, the amount of said substance exhibiting progestin activity being alternately increased in the progestin dominant phases to provide daily unit doses exhibiting progestin dominant activity and decreased in the estrogen dominant phases to provide daily unit doses exhibiting estrogen dominant activity, and wherein the amount of substance exhibiting estrogen activity per unit dose exhibits an estrogen activity equivalent to from about 0.3 to about 2.5 mg of piperazine estrone sulfate, and the amount of substance exhibiting progestin activity per unit dose ranges from 0 to an amount which exhibits a progestin activity equivalent to about 5 mg of norethindrone.

15. A pharmaceutical package according to claim 14, wherein the daily unit doses of said estrogen dominant phases contain an amount of substance exhibiting progestin activity ranging from 0 to an amount which exhibits a progestin activity equivalent to 0.5 mg of norethindrone, and the daily unit doses of said progestin dominant phases contain an amount of substance exhibiting progestin activity which exhibits a progestin activity equivalent to from 0.35 to 5 mg norethindrone, the amount of substance exhibiting progestin activity being greater in said progestin dominant phases than in said estrogen dominant phases.

16. A pharmaceutical package according to claim 14, wherein all of said daily unit doses contain a uniform amount of said substance exhibiting estrogen activity.

17. A pharmaceutical package according to claim 14, wherein the daily unit doses of said estrogen dominant phases are free of substance exhibiting progestin activity.

18. A pharmaceutical package according to claim 14, wherein said substance exhibiting estrogen activity is selected from the group consisting of 17α-ethinyl estradiol, 17βestradiol, 17β-estradiol valerate, conjugated equine estrogens, piperazine estrone sulfate, and estropipate, and said substance exhibiting progestin activity is selected from the group consisting of norethindrone, desogestrel, levo-norgestrel, norgestimate, progesterone, gestodene, cyproterone acetate and medroxy-progesterone acetate.

19. A pharmaceutical package according to claim 14, wherein said daily unit doses are in a form selected from the group consisting of orally administrable form, transdermally administrable form, and buccally administrable form.

20. A pharmaceutical package according to claim 14, containing a series of consecutive daily unit doses arranged in estrogen dominant phases of two daily unit doses each alternating with progestin dominant phases of two daily unit doses each.

21. A pharmaceutical package according to claim 14, containing a series of consecutive daily unit doses arranged in estrogen dominant phases of three daily unit doses each alternating with progestin dominant phases of three daily unit doses each.

22. A pharmaceutical package according to claim 14, containing a hormone replacement therapy preparation, wherein each of said daily unit doses contains an amount of substance exhibiting estrogen activity equivalent to from 0.3 to 2.5 mg of piperazine estrone sulfate, and an amount of substance exhibiting progestin activity ranging from 0 to an amount which exhibits a progestin activity equivalent to 5 mg norethindrone.

23. A pharmaceutical package according to claim 22, wherein each estrogen dominant phase consists of three orally administrable daily unit doses each containing 0.75 mg piperazine estrone sulfate, and each progestin dominant phase consists of three orally administrable daily unit doses each containing 0.75 mg piperazine estrone sulfate and 0.35 mg norethindrone.

24. A pharmaceutical package according to claim 22, wherein each estrogen dominant phase consists of three transdermally administrable daily unit doses each releasing 0.1 mg 17$\beta$-estradiol, and each progestin dominant phase consists of three transdermally administrable daily unit doses each releasing 0.1 mg 17$\beta$-estradiol and 0.35 mg norethindrone.

25. A pharmaceutical package according to claim 22, wherein each estrogen dominant phase consists of three transdermally administrable daily unit doses each releasing 0.1 mg 17$\beta$-estradiol and 0.15 mg norethindrone, and each progestin dominant phase consists of three transdermally administrable daily unit doses each releasing 0.1 mg 17$\beta$-estradiol and 0.35 mg norethindrone.

26. A pharmaceutical package according to claim 22, wherein three unit doses of 1.0 mg of 17$\beta$-estradiol are alternated with three unit doses of 1.0 mg of 17$\beta$-estradiol and 0.35 mg of norethindrone.

* * * * *